(12) United States Patent
Möckel et al.

(10) Patent No.: US 7,306,939 B2
(45) Date of Patent: Dec. 11, 2007

(54) NUCLEOTIDE SEQUENCES ENCODING THE GPM GENE

(75) Inventors: Bettina Möckel, Düsseldorf (DE); Walter Pfefferle, Halle (DE)

(73) Assignee: Degussa GmbH, Dusseldorf (DE)

( * ) Notice: Subject to any disclaimer, the term of this patent is extended or adjusted under 35 U.S.C. 154(b) by 0 days.

(21) Appl. No.: 09/725,178

(22) Filed: Nov. 29, 2000

(65) Prior Publication Data

US 2002/0002275 A1 Jan. 3, 2002

(30) Foreign Application Priority Data

Dec. 2, 1999 (DE) ................................ 199 58 160

(51) Int. Cl.
*C12N 1/20* (2006.01)
*C12N 15/00* (2006.01)
*C12N 9/00* (2006.01)
*C07H 21/02* (2006.01)
*C07H 21/04* (2006.01)

(52) U.S. Cl. .............................. 435/252.32; 435/320.1; 435/183; 435/252.3; 536/23.1; 536/23.2

(58) Field of Classification Search ................ 435/115, 435/233, 183, 320.1, 252.3, 252.32; 536/23.1, 536/23.2, 23.7, 24.3, 24.32, 24.31, 24.33; 530/350

See application file for complete search history.

(56) References Cited

U.S. PATENT DOCUMENTS

2004/0180408 A1* 9/2004 Pompejus et al. ......... 435/69.1

FOREIGN PATENT DOCUMENTS

| EP | 0 197 335 A | 10/1986 |
|----|-------------|---------|
| EP | 0 955 368 A | 11/1999 |
| EP | 1 038 970 A | 9/2000 |
| EP | 1 108 790 | 6/2001 |
| WO | 01 00844 A | 1/2001 |

OTHER PUBLICATIONS

Ngo et al., Computational Complexity, Protein Structure Prediction, and the Levinthal Paradox, in The Protein Folding Problem and Tertiary Structure Prediction, 1994, Merz et al. (ed.), Birkhauser, Boston, MA, pp. 433 and 492-495.*
Sigma Catalog, 1997, p. 1019.*
White P J et al: "Phosphoglycerate Mutase from Streptomyces—Coelicolor A32 Purification and Characterization of Enzyme and Cloning and Sequence Analysis of the Gene"; Journal of Bacteriology, Bd. 174, Nr. 2, 1992, p. 434-440; XP000990937.

* cited by examiner

*Primary Examiner*—Richard Hutson
(74) *Attorney, Agent, or Firm*—Pillsbury Winthrop Shaw Pittman, LLP (57) ABSTRACT

The invention provides nucleotide sequences of the gpm gene which encode phosphoglycerate mutase, and fermentation processes for the preparation of amino acids, especially L-lysine, using corynebacteria wherein the gpm gene is amplified.

10 Claims, 2 Drawing Sheets

Figure 1: Map of plasmid pEC-XK99E

Figure 2: Map of plasmid pXKgpmexp

SEQUENCE LISTING

<160> NUMBER OF SEQ ID NOS: 4

<210> SEQ ID NO 1
<211> LENGTH: 1020
<212> TYPE: DNA
<213> ORGANISM: Corynebacterium glutamicum
<220> FEATURE:

```
<221> NAME/KEY: CDS
<222> LOCATION: (181)..(924)

<400> SEQUENCE: 1
acgcgcatca gaatgggtga agacgccgtc gaacacgcca gaacattctc ctgggcggcc      60
accgccgcac agctatcgtc gctgtacaac gacgctattg ccaacgaaaa tgtcgacggt     120
gaaacgcatc acggctaagt aaacgcgcgt cgtggaacat aaagtggcaa actagtacct     180
```

| atg act aac gga aaa ttg att ctt ctt cgt cac ggt cag agc gaa tgg | 228 |
| Met Thr Asn Gly Lys Leu Ile Leu Leu Arg His Gly Gln Ser Glu Trp | |
| 1               5                   10                  15      | |

| aac gca tcc aac cag ttc act gga tgg gtc gac gtc aat ctg acc gaa | 276 |
| Asn Ala Ser Asn Gln Phe Thr Gly Trp Val Asp Val Asn Leu Thr Glu | |
|         20                  25                  30              | |

| cag ggt gag gct gag gcc aag cgc gga ggc gaa ctc ctc gtc gag gca | 324 |
| Gln Gly Glu Ala Glu Ala Lys Arg Gly Gly Glu Leu Leu Val Glu Ala | |
|     35                  40                  45                  | |

| ggc gtc ctc cca ggc gtt gta tac acc tcc ttg ctg cgt cgc gcg atc | 372 |
| Gly Val Leu Pro Gly Val Val Tyr Thr Ser Leu Leu Arg Arg Ala Ile | |
| 50                  55                  60                      | |

| cgc act gca aac atc gca ctg aac gct gca gac cgc cac tgg atc cca | 420 |
| Arg Thr Ala Asn Ile Ala Leu Asn Ala Ala Asp Arg His Trp Ile Pro | |
| 65              70                  75                  80      | |

| gtg atc cgc gac tgg cgc ctc aac gag cgt cac tac ggc gca ctg cag | 468 |
| Val Ile Arg Asp Trp Arg Leu Asn Glu Arg His Tyr Gly Ala Leu Gln | |
|                 85                  90                  95      | |

| ggc ctt gac aag gct gca acc aag gaa aaa tac ggc gac gac cag ttc | 516 |
| Gly Leu Asp Lys Ala Ala Thr Lys Glu Lys Tyr Gly Asp Asp Gln Phe | |
|             100                 105                 110         | |

| atg gaa tgg cgc cgc tcc tac gac acc cca cca cca gag ctc gcg gat | 564 |
| Met Glu Trp Arg Arg Ser Tyr Asp Thr Pro Pro Pro Glu Leu Ala Asp | |
|         115                 120                 125             | |

| gac gca gag tac tcc cag gca aat gac cct cgt tac gcg gac ctc gac | 612 |
| Asp Ala Glu Tyr Ser Gln Ala Asn Asp Pro Arg Tyr Ala Asp Leu Asp | |
|     130                 135                 140                 | |

| gta gtt cca cgc acc gaa tgc ctc aag gac gtt gtg gtt cgt ttt gtt | 660 |
| Val Val Pro Arg Thr Glu Cys Leu Lys Asp Val Val Val Arg Phe Val | |
| 145                 150                 155                 160 | |

| cct tac ttc gag gaa gaa atc ctg cca cgc gca aag aag ggc gaa acc | 708 |
| Pro Tyr Phe Glu Glu Glu Ile Leu Pro Arg Ala Lys Lys Gly Glu Thr | |
|                 165                 170                 175     | |

| gtc ctc atc gca gca cac ggc aac tcc ctg cgt gcg ctg gtt aag cac | 756 |
| Val Leu Ile Ala Ala His Gly Asn Ser Leu Arg Ala Leu Val Lys His | |
|             180                 185                 190         | |

| ctt gac ggc atc tcc gat gct gat atc gca gag ctc aac atc cca acc | 804 |
| Leu Asp Gly Ile Ser Asp Ala Asp Ile Ala Glu Leu Asn Ile Pro Thr | |
|         195                 200                 205             | |

| ggc atc cca ctg gtc tac gaa atc gcc gaa gac ggt tcc gta gta aac | 852 |
| Gly Ile Pro Leu Val Tyr Glu Ile Ala Glu Asp Gly Ser Val Val Asn | |
|     210                 215                 220                 | |

| cca ggc ggc acc tac ctc gat cct gag gca gca gca gcc ggc gca gca | 900 |
| Pro Gly Gly Thr Tyr Leu Asp Pro Glu Ala Ala Ala Ala Gly Ala Ala | |
| 225                 230                 235                 240 | |

| gca gta gca aac cag ggt aat aag tagctatttg taggtgagca ctcttcttgc | 954 |
| Ala Val Ala Asn Gln Gly Asn Lys | |
|                 245 | |

```
tttcgtattg ggcgtggtcc tcatgggcct cgccctacct gcgtatacga aaattaaaga    1014
tcggat                                                               1020
```

<210> SEQ ID NO 2
<211> LENGTH: 248
<212> TYPE: PRT
<213> ORGANISM: Corynebacterium glutamicum

<400> SEQUENCE: 2

Met Thr Asn Gly Lys Leu Ile Leu Leu Arg His Gly Gln Ser Glu Trp
1               5                   10                  15

Asn Ala Ser Asn Gln Phe Thr Gly Trp Val Asp Val Asn Leu Thr Glu
            20                  25                  30

Gln Gly Glu Ala Glu Ala Lys Arg Gly Gly Glu Leu Leu Val Glu Ala
        35                  40                  45

Gly Val Leu Pro Gly Val Val Tyr Thr Ser Leu Leu Arg Arg Ala Ile
    50                  55                  60

Arg Thr Ala Asn Ile Ala Leu Asn Ala Ala Asp Arg His Trp Ile Pro
65                  70                  75                  80

Val Ile Arg Asp Trp Arg Leu Asn Glu Arg His Tyr Gly Ala Leu Gln
                85                  90                  95

Gly Leu Asp Lys Ala Ala Thr Lys Glu Lys Tyr Gly Asp Asp Gln Phe
            100                 105                 110

Met Glu Trp Arg Arg Ser Tyr Asp Thr Pro Pro Glu Leu Ala Asp
        115                 120                 125

Asp Ala Glu Tyr Ser Gln Ala Asn Asp Pro Arg Tyr Ala Asp Leu Asp
    130                 135                 140

Val Val Pro Arg Thr Glu Cys Leu Lys Asp Val Val Arg Phe Val
145                 150                 155                 160

Pro Tyr Phe Glu Glu Glu Ile Leu Pro Arg Ala Lys Lys Gly Glu Thr
                165                 170                 175

Val Leu Ile Ala Ala His Gly Asn Ser Leu Arg Ala Leu Val Lys His
            180                 185                 190

Leu Asp Gly Ile Ser Asp Ala Asp Ile Ala Glu Leu Asn Ile Pro Thr
        195                 200                 205

Gly Ile Pro Leu Val Tyr Glu Ile Ala Glu Asp Gly Ser Val Val Asn
    210                 215                 220

Pro Gly Gly Thr Tyr Leu Asp Pro Glu Ala Ala Ala Gly Ala Ala
225                 230                 235                 240

Ala Val Ala Asn Gln Gly Asn Lys
            245

<210> SEQ ID NO 3
<211> LENGTH: 20
<212> TYPE: DNA
<213> ORGANISM: PCR primer

<400> SEQUENCE: 3
taaagtggca aactagtacc                                              20

<210> SEQ ID NO 4
<211> LENGTH: 19
<212> TYPE: DNA
<213> ORGANISM: PCR primer

<400> SEQUENCE: 4
ctacttatta ccctggttt                                               19

US 7,306,939 B2

NUCLEOTIDE SEQUENCES ENCODING THE GPM GENE

The invention provides nucleotide sequences encoding the gpm gene, which encodes phosphoglycerate mutase, and fermentation processes for the preparation of amino acids, especially L-lysine, using corynebacteria in which the gpm gene is amplified.

BACKGROUND OF THE INVENTION

1. Field of the Invention

The invention provides nucleotide sequences encoding the gpm gene and fermentation processes for the preparation of amino acids, especially L-lysine, using corynebacteria in which the gpm gene is amplified.

2. Background Information

Amino acids, especially L-lysine, are used in human medicine and in the pharmaceutical industry, but especially in animal nutrition.

It is known that amino acids are prepared by the fermentation of strains of corynebacteria, especially Corynebacterium glutamicum. Because of its great importance, attempts are constantly being made to improve the preparative processes. Improvements to the processes may relate to measures involving the fermentation technology, for example, stirring and oxygen supply, or the composition of the nutrient media, for example, the sugar concentration during fermentation, or the work-up to the product form, for example, by ion exchange chromatography, or the intrinsic productivity characteristics of the microorganism itself.

The productivity characteristics of these microorganisms are improved by using methods of mutagenesis, selection and mutant choice to give strains which are resistant to antimetabolites, for example, the lysine analogue S-(2-aminoethyl)cysteine, or auxotrophic for metabolites important in regulation, and produce L-lysine.

Methods of recombinant DNA technology have also been used for some years to improve amino acid-producing strains of Corynebacterium by amplifying individual amino acid biosynthesis genes and studying the effect on amino acid production. Review articles on this subject have been published inter alia by Kinoshita ("Glutamic Acid Bacteria", in: Biology of Industrial Microorganisms, Demain and Solomon (Eds.), Benjamin Cummings, London, UK, 1985, 115-142), Hilliger (BioTec 2, 40-44 (1991)), Eggeling (Amino Acids 6, 261-272 (1994)), Jetten and Sinskey (Critical Reviews in Biotechnology 15, 73-103 (1995)) and Sahm et al. (Annals of the New York Academy of Science 782, 25-39 (1996)).

SUMMARY OF THE INVENTION

Object of the Invention

It is an object of the invention to provide novel means for improving the preparation of amino acids, especially L-lysine, by fermentation.

DESCRIPTION OF THE INVENTION

Amino acids, especially L-lysine, are used in human medicine, in the pharmaceutical industry and particularly in animal nutrition. It is therefore of general interest to provide novel improved processes for the preparation of amino acids, especially L-lysine.

When L-lysine or lysine is mentioned hereafter, it is understood as meaning not only the base but also the salts, for example, lysine monohydrochloride or lysine sulfate.

The invention provides an isolated polynucleotide from corynebacteria which contains a polynucleotide sequence selected from the group comprising:
  a) a polynucleotide which is at least 70% identical to a polynucleotide encoding a polypeptide containing the amino acid sequence of SEQ ID NO:2,
  b) a polynucleotide encoding a polypeptide containing an amino acid sequence which is at least 70% identical to the amino acid sequence of SEQ ID NO:2,
  c) a polynucleotide which is complementary to the polynucleotides of a) or b), and
  d) a polynucleotide containing at least 15 consecutive bases of the polynucleotide sequence of a), b) or c).

The invention also provides the polynucleotide with the aforementioned features which is preferably a replicatable DNA containing:
  (i) the nucleotide sequence shown in SEQ ID NO:1, or
  (ii) at least one sequence corresponding to sequence (i) within the degeneracy of the genetic code, or
  (iii) at least one sequence which hybridizes with the sequence complementary to sequence (i) or (ii), and optionally
  (iv) neutral sense mutations in (i).

Figure 2:
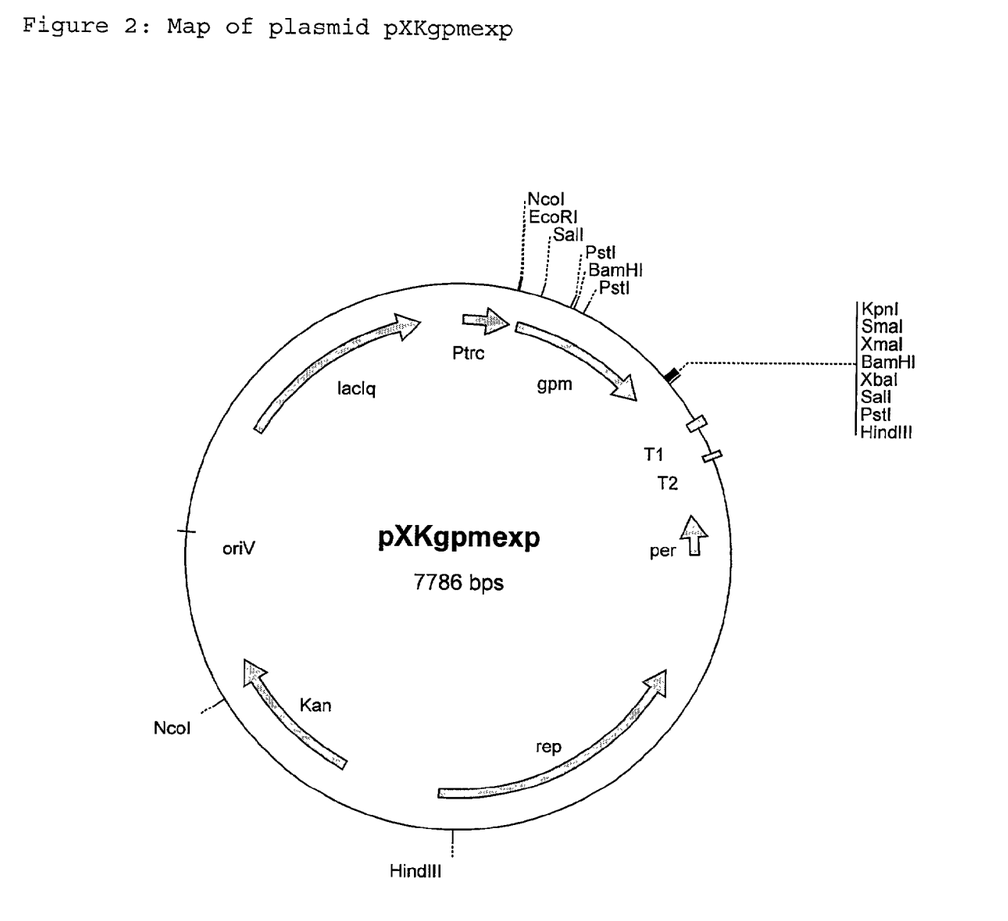
FIG. 2: Map of plasmid PxKgpmexp

The invention also provides:
  a polynucleotide with features a)-d)containing the nucleotide sequence as shown in SEQ ID NO:1,
  a polynucleotide with features a)-d)encoding a polypeptide containing the amino acid sequence as shown in SEQ ID NO:2,
  a vector containing the polynucleotide described above, especially shuttle vector or plasmid vector pXKgpmexp, which is shown in FIG. 2, and
  corynebacteria, serving as host cells, which contain the vector or in which the gpm gene is amplified.

The invention also provides polynucleotides consisting substantially of a polynucleotide sequence which is obtainable by screening, by means of hybridization, of an appropriate gene library, containing the complete gene with the polynucleotide sequence corresponding to SEQ ID NO:1, with a probe containing the sequence of said polynucleotide according to SEQ ID NO:1 or a fragment thereof, and by isolation of said DNA sequence.

As hybridization probes for RNA, cDNA and DNA, polynucleotide sequences according to the invention are suitable for isolating the full length of cDNAs coding for phosphoglycerate mutase, and for isolating cDNAs or genes whose sequence exhibits a high degree of similarity to the sequence of the phosphoglycerate mutase gene.

Polynucleotide sequences according to the invention are further suitable as primers for the preparation, by the polymerase chain reaction (PCR), of DNA of genes coding for phosphoglycerate mutase.

Such oligonucleotides serving as probes or primers contain at least 30, preferably at least 20 and very particularly preferably at least 15 consecutive bases. Oligonucleotides with a length of at least 40 or 50 base pairs are also suitable.

"Isolated" means separated from its natural environment.

"Polynucleotide" refers in general to polyribonucleotides and polydeoxyribonucleotides, it being possible for the RNAs or DNAs in question to be unmodified or modified.

"Polypeptides" are understood as meaning peptides or proteins containing two or more amino acids bonded via peptide linkages.

The polypeptides according to the invention include a polypeptide according to SEQ ID NO:2, especially those with the biological activity of phosphoglycerate mutase and also those which are at least 70% identical to the polypeptide according to SEQ ID NO:2, preferably at least 80% and particularly at least 90% to 95% identical to the polypeptide according to SEQ ID NO:2, and have said activity.

The invention further relates to a fermentation process for the preparation of amino acids, especially L-lysine, using corynebacteria which, in particular, already produce an amino acid and in which the nucleotide sequences encoding the gpm gene are amplified and, in particular, overexpressed.

In this context the term "amplification" describes the increase in the intracellular activity, in a microorganism, of one or more enzymes which are encoded by the appropriate DNA, for example by increasing the copy number of the gene(s), using a strong promoter or using a gene encoding an appropriate enzyme with a high activity, and optionally combining these measures.

The microorganisms provided by the present invention can produce L-amino acids, especially L-lysine, from glucose, sucrose, lactose, fructose, maltose, molasses, starch or cellulose or from glycerol and ethanol. Said microorganisms can be representatives of corynebacteria, especially of the genus Corynebacterium. The species *Corynebacterium glutamicum* may be mentioned in particular in the genus Corynebacterium, being known to those skilled in the art for its ability to produce L-amino acids.

The following known wild-type strains:
*Corynebacterium glutamicum* ATCC13032
*Corynebacterium acetoglutamicum* ATCC15806
*Corynebacterium acetoacidophilum* ATCC13870
*Corynebacterium thermoaminogenes* FERM BP-1539
*Corynebacterium melassecola* ATCC17965
*Brevibacterium flavum* ATCC14067
*Brevibacterium lactofermentum* ATCC13869 and
*Brevibacterium divaricatum* ATCC14020 and L-lysine-producing mutants or strains prepared therefrom, such as:
*Corynebacterium glutamicum* FERM-P 1709
*Brevibacterium flavum* FERM-P 1708
*Brevibacterium lactofermentum* FERM-P 1712
*Corynebacterium glutamicum* FERM-P 6463
*Corynebacterium glutamicum* FERM-P 6464 and
*Corynebacterium glutamicum* DSM5715 are examples of suitable strains of the genus Corynebacterium, especially of the species *Corynebacterium glutamicum*.

The inventors have succeeded in isolating, from *C. glutamicum*, the novel gpm gene coding for the enzyme phosphoglycerate mutase (EC 5.4.2.1).

The first step in isolating the gpm gene or other genes from *C. glutamicum* is to construct a gene library of this microorganism in *E. coli*. The construction of gene libraries is documented in generally well-known textbooks and handbooks. Examples which may be mentioned are the textbook by Winnacker entitled From Genes to Clones, Introduction to Gene Technology (Verlag Chemie, Weinheim, Germany, 1990) or the handbook by Sambrook et al. entitled Molecular Cloning, A Laboratory Manual (Cold Spring Harbor Laboratory Press, 1989). A very well-known gene library is that of the *E. coli* K-12 strain W3110, which was constructed by Kohara et al. (Cell 50, 495-508 (1987)) in .lambda. vectors. Bathe et al. (Molecular and General Genetics 252, 255-265, 1996) describe a gene library of *C. glutamicum* ATCC13032, which was constructed using cosmid vector SuperCos I (Wahl et al., 1987, Proceedings of the National Academy of Sciences USA 84, 2160-2164) in the *E. coli* K-12 strain NM554 (Raleigh et al., 1988, Nucleic Acids Research 16, 1563-1575). Bormann et al., 1992, (Molecular Microbiology 6(3), 317-326) in turn describe a gene library of *C. glutamicum* ATCC13032 using cosmid pHC79 (Hohn and Collins, Gene 11, 291-298 (1980)). A gene library of *C. glutamicum* in *E. coli* can also be constructed using plasmids like pBR322 (Bolivar, Life Sciences 25, 807-818 (1979)) or pUC9 (Viera et al., 1982, Gene 19, 259-268). Restriction- and recombination-defective *E. coli* strains are particularly suitable as hosts, an example being the strain DH5.alpha.mcr, which has been described by Grant et al. (Proceedings of the National Academy of Sciences USA 87 (1990) 4645-4649). The long DNA fragments cloned with the aid of cosmids can then in turn be subcloned into common vectors suitable for sequencing, and subsequently sequenced, e.g. as described by Sanger et al. (Proceedings of the National Academy of Sciences of the United States of America 74, 5463-5467, 1977).

The novel DNA sequence of *C. glutamicum* coding for the gpm gene, which as SEQ ID NO:1 forms part of the present invention, was obtained in this way. Furthermore, the amino acid sequence of the corresponding protein was derived from said DNA sequence by the methods described above. The resulting amino acid sequence of the gpm gene product is shown in SEQ ID NO:2.

Coding DNA sequences which result from SEQ ID NO:1 due to the degeneracy of the genetic code also form part of the invention. Likewise, DNA sequences which hybridize with SEQ ID NO:1 or portions of SEQ ID NO:1 form part of the invention. Furthermore, conservative amino acid exchanges, for example, the exchange of glycine for alanine or of aspartic acid for glutamic acid in proteins, are known to those skilled in the art as "sense mutations", which do not cause a fundamental change in activity of the protein, i.e. they are neutral. It is also known that changes at the N- and/or C-terminus of a protein do not substantially impair its function or may even stabilize it. Those skilled in the art will find information on this subject inter alia in Ben-Bassat et al. (Journal of Bacteriology 169, 751-757 (1987)), O'Regan et al. (Gene 77, 237-251 (1989)), Sahin-Toth et al. (Protein Sciences 3, 240-247 (1994)) and Hochuli et al. (Bio/Technology 6, 1321-1325 (1988)) and in well-known textbooks on genetics and molecular biology. Amino acid sequences which correspondingly result from SEQ ID NO:2 also form part of the invention.

Likewise, DNA sequences which hybridize with SEQ ID NO:1 or portions of SEQ ID NO:1 form part of the invention. Finally, DNA sequences which are prepared by the polymerase chain reaction (PCR) using primers resulting from SEQ ID NO:1 form part of the invention. Such oligonucleotides typically have a length of at least 15 base pairs.

Those skilled in the art will find instructions on the identification of DNA sequences by means of hybridization in the handbook "The DIG System Users Guide for Filter Hybridization" from Boehringer Mannheim GmbH (Mannheim, Germany, 1993) and in Liebl et al. (International Journal of Systematic Bacteriology (1991) 41, 255-260), inter alia. Those skilled in the art will find instructions on the amplification of DNA sequences with the aid of the polymerase chain reaction (PCR) in the handbook by Gait entitled Oligonucleotide synthesis: a practical approach (IRL Press, Oxford, UK, 1984) and in Newton and Graham: PCR (Spektrum Akademischer Verlag, Heidelberg, Germany, 1994), inter alia.

The inventors have discovered that, after overexpression of the gpm gene, the production of amino acids, especially L-lysine, by corynebacteria is improved.

Overexpression can be achieved by increasing the copy number of the appropriate genes or mutating the promoter and regulatory region or the ribosome binding site located upstream from the structural gene. Expression cassettes incorporated upstream from the structural gene work in the same way. Inducible promoters additionally make it possible to increase the expression in the course of the production of L-lysine by fermentation. Measures for prolonging the life of the mRNA also improve the expression. Furthermore, the enzyme activity is also enhanced by preventing the degradation of the enzyme protein. The genes or gene constructs can either be located in plasmids of variable copy number or integrated and amplified in the chromosome. Alternatively, it is also possible to achieve overexpression of the genes in question by changing the composition of the media and the culture technique.

Those skilled in the art will find relevant instructions in Martin et al. (Bio/Technology 5, 137-146 (1987)), Guerrero et al. (Gene 138, 35-41 (1994)), Tsuchiya and Morinaga (Bio/Technology 6, 428-430 (1988)), Eikmanns et al. (Gene 102, 93-98 (1991)), European patent EP 0 472 869, U.S. Pat. No. 4,601,893, Schwarzer and Puhler (Bio/Technology 9, 84-87 (1991)), Reinscheid et al. (Applied and Environmental Microbiology 60, 126-132 (1994)), LaBarre et al. (Journal of Bacteriology 175, 1001-1007 (1993)), patent application WO 96/15246, Malumbres et al. (Gene 134, 15-24 (1993)), Japanese Offenlegungsschrift JP-A-10-229891, Jensen and Hammer (Biotechnology and Bioengineering 58, 191-195 (1998)) and Makrides (Microbiological Reviews 60, 512-538 (1996)) and in well-known textbooks on genetics and molecular biology, inter alia. For example, the gpm gene according to the invention has been overexpressed with the aid of plasmids.

Suitable plasmids are those which are replicated in corynebacteria. Numerous known plasmid vectors, for example, pZ1 (Menkel et al., Applied and Environmental Microbiology (1989) 64, 549-554), pEKEx1 (Eikmanns et al., Gene 102, 93-98 (1991)) or pHS2-1 (Sonnen et al., Gene 107, 69-74 (1991)), are based on cryptic plasmids pHM1519, pBL1 or pGA1. Other plasmid vectors, for example, those based on pCG4 (U.S. Pat. No. 4,489,160), pNG2 (Serwold-Davis et al., FEMS Microbiology Letters 66, 119-124 (1990)) or pAG1 (U.S. Pat. No. 5,158,891), can be used in the same way.

An example of a plasmid which can be used for overexpression of the gpm gene is E. coli/C. glutamicum shuttle expression vector pXKgpmexp. The vector contains the replication region rep of plasmid pGA1, including the replication effector per (U.S. Pat. No. 5,175,108; Nesvera et al., Journal of Bacteriology 179, 1525-1532 (1997)), the kanamycin resistance gene aph(3')-IIa from Escherichia coli, the origin of replication, the trc promoter, the termination regions T1 and T2, the lacI$^q$ gene (repressor of the lac operon of E. coli) and a multiple cloning site mcs (Norrander, J. M. et al., Gene 26, 101-106 (1983)) of plasmid pTRC99A (Amann et al. (1988), Gene 69, 301-315).

Shuttle expression vector pXKgpmexp is shown in FIG. 2.

In addition it can be advantageous for the production of amino acids, especially L-lysine, to overexpress not only the gpm gene but also one or more enzymes of the particular biosynthetic pathway, the glycolysis, the anaplerosis, the citric acid cycle or the amino acid export.

Thus, for example, the following can be overexpressed for the preparation of L-lysine:
  simultaneously the dapA gene coding for dihydrodipicolinate synthase (EP-B-0 197 335), or
  simultaneously the gap gene coding for glyceraldehyde 3-phosphate dehydrogenase (Eikmanns (1992), Journal of Bacteriology 174, 6076-6086), or
  simultaneously the tpi gene coding for triose phosphate isomerase (Eikmanns (1992), Journal of Bacteriology 174, 6076-6086), or
  simultaneously the pgk gene coding for 3-phosphoglycerate kinase (Eikmanns (1992), Journal of Bacteriology 174, 6076-6086), or
  simultaneously the pyc gene coding for pyruvate carboxylase (Eikmanns (1992), Journal of Bacteriology 174, 6076-6086), or
  simultaneously the lysE gene coding for lysine export (DE-A-195 48 222), or
  simultaneously the mqo gene coding for malate quinone oxidoreductase (Molenaar et al. (1998), European Journal of Biochemistry 254, 395-403), or
  the zwa1 gene (DE 199 59 328.0, DSM13115).

In addition to amplification of the gpm gene, it can also be advantageous for the production of amino acids, especially L-lysine, simultaneously to attenuate the following:
  the pck gene coding for phosphoenol pyruvate carboxykinase (DE 199 50 409.1, DSM13047), or
  the pgi gene coding for glucose 6-phosphate isomerase (U.S. Ser. No. 09/396,478, DSM12969), or
  the poxB gene coding for pyruvate oxidase (DE 199 51 975.7, DSM13114), or
  the zwa2 gene (DE 199 59 327.2, DSM13113).

It can also be advantageous for the production of amino acids, especially L-lysine, not only to overexpress the gpm gene but also to switch off undesirable secondary reactions (Nakayama: "Breeding of Amino Acid Producing Microorganisms", in: Overproduction of Microbial Products, Krumphanzl, Sikyta, Vanek (eds.), Academic Press, London, UK, 1982).

The microorganisms prepared according to the invention can be cultivated for the production of amino acids, especially L-lysine, continuously or discontinuously by the batch process, the fed batch process or the repeated fed batch process. A summary of known cultivation methods is described in the textbook by Chmiel (Bioprozesstechnik 1. Einführung in die Bioverfahrenstechnik (Bioprocess Technology 1. Introduction to Bioengineering) (Gustav Fischer Verlag, Stuttgart, 1991)) or in the textbook by Storhas (Bioreaktoren und periphere Einrichtungen (Bioreactors and Peripheral Equipment) (Vieweg Verlag, Brunswick/Wiesbaden, 1994)).

The culture medium to be used must appropriately meet the demands of the particular strains. Descriptions of culture media for various microorganisms can be found in the handbook "Manual of Methods for General Bacteriology" of the American Society for Bacteriology (Washington D.C., USA, 1981). Carbon sources which can be used are sugars and carbohydrates, for example, glucose, sucrose, lactose, fructose, maltose, molasses, starch and cellulose, oils and fats, for example, soya oil, sunflower oil, groundnut oil and coconut fat, fatty acids, for example, palmitic acid, stearic acid and linoleic acid, alcohols, for example, glycerol and ethanol, and organic acids, for example, acetic acid. These substances can be used individually or as a mixture. Nitrogen sources which can be used are organic nitrogen-containing compounds such as peptones, yeast extract, meat extract, malt extract, corn steep liquor, soya bean flour and urea, or inorganic compounds such as ammonium sulfate, ammonium chloride, ammonium phosphate, ammonium carbonate and ammonium nitrate. The nitrogen sources can be used individually or as a mixture. Phosphorus sources which can be used are phosphoric acid, potassium dihydrogenphosphate or dipotassium hydrogenphosphate or the corresponding sodium salts. The culture medium must also contain metal salts, for example, magnesium sulfate or iron sulfate, which are necessary for growth. Finally, essential growth-promoting substances such as amino acids and vitamins can be used in addition to the substances mentioned above. Suitable precursors can also be added to the culture medium. Said feed materials can be added to the culture all at once or fed in appropriately during cultivation.

The pH of the culture is controlled by the appropriate use of basic compounds such as sodium hydroxide, potassium hydroxide, ammonia or aqueous ammonia, or acid compounds such as phosphoric acid or sulfuric acid. Foaming can be controlled using antifoams such as fatty acid polyglycol esters. The stability of plasmids can be maintained by adding suitable selectively acting substances, for example, antibiotics, to the medium. Aerobic conditions are maintained by introducing oxygen or oxygen-containing gaseous mixtures, for example, air, into the culture. The temperature of the culture is normally 20° C. to 45° C. and preferably 25° C. to 40° C. The culture is continued until L-lysine formation has reached a maximum. This objective is normally achieved within 10 hours to 160 hours.

L-lysine can be analyzed by anion exchange chromatography with subsequent ninhydrin derivatization, as described by Spackman et al. (Analytical Chemistry 30 (1958) 1190).

The following microorganisms were deposited in the Deutsche Sammlung fur Mikroorganismen und Zellkulturen (German Collection of Microorganisms and Cell Cultures (DSMZ), Deutsche Sammlung von Mikroorganismen und Zelikulturen GmbH, Inhoffenstraβe7 B, 38124 Braunschweig, Germany on Jul. 4, 2000 under the terms of the Budapest Treaty:

Corynebacterium glutamicum strain DSM5715/pXKgpmexp as DSM13456
Corynebacterium glutamicum strain DSM5715/pEC-XK as DSM13455

The fermentation process according to the invention is used for the preparation of amino acids, especially L-lysine.

The abbreviations and symbols are defined as follows:

| | |
|---|---|
| per: | copy of number control gene from pGA1 |
| oriE: | plasmid-coded origin of replication from E. coli |
| rep: | plasmid-coded origin of replication from C. glutamicum plasmid pGA1 |
| Ptrc: | trc promoter from pTRC99A |
| T1, T2: | terminator regions 1 and 2 from pTRC99A |
| lacIq: | repressor gene of the lac operon |
| Kan: | kanamycin resistance gene |
| gpm: | gpm gene from C. glutamicum, which encodes phosphoglycerate mutase |
| EcoRI: | cleavage site of the restriction enzyme EcoRI |
| Ec1136II | cleavage site of the restriction enzyme ec1136II |
| HindIII | cleavage site of the restriction enzyme HindIII |
| KpnI: | cleavage site of the restriction enzyme KpnI |
| SalI: | cleavage site of the restriction enzyme SalI |
| SmaI: | cleavage site of the restriction enzyme SmaI |
| PstI: | cleavage site of the restriction enzyme PstI |

-continued

| | |
|---|---|
| BamHI: | cleavage site of the restriction enzyme BamHI |
| NcoI: | cleavage site of the restriction enzyme NcoI |
| XbaI: | cleavage site of the restriction enzyme XbaI |
| XmaI: | cleavage site of the restriction enzyme XmaI |
| SacI: | cleavage site of the restriction enzyme SacI |

DETAILED DESCRIPTION OF THE INVENTION

The present invention is illustrated in greater detail below with the aid of Examples.

EXAMPLE 1

Preparation of a Genomic Cosmid Gene Library From *Corynebacterium glutamicum* ATCC13032

Chromosomal DNA from *Corynebacterium glutamicum* ATCC13032 was isolated as described by Tauch et al. (1995, Plasmid 33, 168-179) and partially cleaved with the restriction enzyme Sau3AI (Amersham Pharmacia, Freiburg, Germany, product description Sau3AI, code no. 27-0913-02). The DNA fragments were dephosphorylated with shrimp alkaline phosphatase (Roche Molecular Biochemicals, Mannheim, Germany, product description SAP, code no. 1758250). The DNA of cosmid vector SuperCos1 (Wahl et al. (1987) Proceedings of the National Academy of Sciences USA 84, 2160-2164), obtained from Stratagene (La Jolla, USA, product description SuperCos1 Cosmid Vector Kit, code no. 251301), was cleaved with the restriction enzyme XbaI (Amersham Pharmacia, Freiburg, Germany, product description XbaI, code no. 27-0948-02) and also dephosphorylated with shrimp alkaline phosphatase. The cosmid DNA was then cleaved with the restriction enzyme BamHI (Amersham Pharmacia, Freiburg, Germany, product description BamHI, code no. 27-0868-04). The cosmid DNA treated in this way was mixed with the treated ATCC13032 DNA and the mixture was treated with T4 DNA ligase (Amersham Pharmacia, Freiburg, Germany, product description T4 DNA ligase, code no. 27-0870-04). The ligation mixture was then packaged into phages using Gigapack II XL Packing Extract (Stratagene, La Jolla, USA, product description Gigapack II XL Packing Extract, code no. 200217). For infection of the *E. coli* strain NM554 (Raleigh et al., 1988, Nucleic Acids Research 16, 1563-1575), the cells were taken up in 10 mM MgSO$_4$ and mixed with an aliquot of the phage suspension. Infection and titering of the cosmid library were carried out as described by Sambrook et al. (1989, Molecular Cloning: A Laboratory Manual, Cold Spring Harbor), the cells being plated on LB agar (Lennox, 1955, Virology 1, 190) containing 100 mg/l of ampicillin. After incubation overnight at 37° C., recombinant single clones were selected.

EXAMPLE 2

Isolation and Sequencing of the gpm Gene

The cosmid DNA of a single colony was isolated with the Qiaprep Spin Miniprep Kit (product no. 27106, Qiagen, Hilden, Germany) in accordance with the manufacturer's instructions and partially cleaved with the restriction enzyme Sau3AI (Amersham Pharmacia, Freiburg, Germany, product description Sau3AI, product no. 27-0913-02). The DNA fragments were dephosphorylated with shrimp alkaline phosphatase (Roche Molecular Biochemicals, Mannheim, Germany, product description SAP, product no. 1758250). After separation by gel electrophoresis, the cosmid fragments in the size range from 1500 to 2000 bp were isolated with the QiaExII Gel Extraction Kit (product no. 20021, Qiagen, Hilden, Germany). The DNA of sequencing vector pZero-1, obtained from Invitrogen (Groningen, The Netherlands, product description Zero Background Cloning Kit, product no. K2500-01), was cleaved with the restriction enzyme BamHI (Amersham Pharmacia, Freiburg, Germany, product description BamHI, product no. 27-0868-04). Ligation of the cosmid fragments into sequencing vector pZero-1 was carried out as described by Sambrook et al. (1989, Molecular Cloning: A Laboratory Manual, Cold Spring Harbor), the DNA mixture being incubated overnight with T4 ligase (Pharmacia Biotech, Freiburg, Germany). This ligation mixture was then introduced into the *E. coli* strain DH5αMCR (Grant, 1990, Proceedings of the National Academy of Sciences USA 87, 4645-4649) by electroporation (Tauch et al. 1994, FEMS Microbiol. Letters 123, 343-7) and plated on LB agar (Lennox, 1955, Virology 1, 190) containing 50 mg/l of zeocin. Plasmid preparation of the recombinant clones was carried out with Biorobot 9600 (product no. 900200, Qiagen, Hilden, Germany). Sequencing was carried out by the dideoxy chain termination method of Sanger et al. (1977, Proceedings of the National Academy of Sciences USA 74, 5463-5467) with modifications by Zimmermann et al. (1990, Nucleic Acids Research 18, 1067). The "RR dRhodamine Terminator Cycle Sequencing Kit" from PE Applied Biosystems (product no. 403044, Weiterstadt, Germany) was used. Separation by gel electrophoresis and analysis of the sequencing reaction were carried out in a "Rotiphorese NF acrylamide/bisacrylamide" gel (29:1) (product no. A124.1, Roth, Karlsruhe, Germany) with the "ABI Prism 377" sequencer from PE Applied Biosystems (Weiterstadt, Germany).

The raw sequence data obtained were then processed using the Staden programming package (1986, Nucleic Acids Research 14, 217-231), version 97-0. The individual sequences of the pzero-1 derivatives were assembled into a cohesive contig. Computer-assisted coding region analysis was performed with the XNIP program (Staden, 1986, Nucleic Acids Research 14, 217-231). Further analyses were performed with the "BLAST search programs" (Altschul et al., 1997, Nucleic Acids Research 25, 3389-3402) against the non-redundant data bank of the "National Center for Biotechnology Information" (NCBI, Bethesda, Md., USA).

The nucleotide sequence obtained is shown in SEQ ID NO:1. Analysis of the nucleotide sequence gave an open reading frame of 744 base pairs, which was called the gpm gene. The gpm gene codes for a protein of 248 amino acids.

EXAMPLE 3

Preparation of Shuttle Expression Vector pXKgmpexp for Amplification of the gpm Gene in *C. glutamicum*

3.1. Cloning of the gpm Gene

Chromosomal DNA was isolated from the strain ATCC13032 by the method of Eikmanns et al. (Microbiology 140, 1817-1828 (1994)). On the basis of the sequence of the gpm gene known for *C. glutamicum* from Example 2, the following oligonucleotides were chosen for the polymerase chain reaction:

Gpm (ex1.1):
5' TAA AGT GGC AAA CTA GTACC 3'(SEQ ID NO:3)
Gpm (ex2):
5' CTA CTT ATT ACC CTG GTT T 3'(SEQ ID NO:4)

The primers shown were synthesized by ARK Scientific GmbH Biosystems (Darmstadt, Germany) and PCR was carried out by the standard PCR method of Innis et al. (PCR protocols. A guide to methods and applications, 1990, Academic Press) with Pwo polymerase from Roche Diagnostics GmbH (Mannheim, Germany). Using the polymerase chain reaction, the primers allow the amplification of an approx. 0.77 kb DNA fragment carrying the gpm gene.

The approx. 0.77 kb gpm fragment was isolated from the agarose gel with the QiaExII Gel Extraction Kit (product no. 20021, Qiagen, Hilden, Germany).

3.2. Construction of Shuttle Vector pEC-XK99E

*E. coli/C. glutamicum* shuttle vector pEC-XK99E was constructed according to the state of the art. The vector contains the replication region rep of plasmid pGA1, including the replication effector per (U.S. Pat. No. 5,175,108; Nesvera et al., Journal of Bacteriology 179, 1525-1532 (1997)), the kanamycin resistance gene aph(3')-IIa from *Escherichia coli* (Beck et al. (1982), Gene 19, 327-336), the origin of replication, the trc promoter, the termination regions T1 and T2, the lacI$^q$ gene (repressor of the lac operon of *E. coli*) and a multiple cloning site mcs (Norrander, J. M. et al., Gene 26, 101-106 (1983)) of plasmid pTRC99A (Amann et al. (1988), Gene 69, 301-315).

The constructed *E. coli/C. glutamicum* shuttle vector pEC-XK99E was transferred to *C. glutamicum* DSM5715 by electroporation (Liebl et al., 1989, FEMS Microbiology Letters 53, 299-303). The transformants were selected on LBHIS agar consisting of 18.5 g/l of brain-heart infusion broth, 0.5 M sorbitol, 5 g/l of bacto tryptone, 2.5 g/l of bacto yeast extract, 5 g/l of NaCl and 18 g/l of bacto agar, which had been supplemented with 25 mg/l of kanamycin. Incubation was carried out for 2 days at 33° C.

Plasmid DNA was isolated from one transformant by the conventional methods (Peters-Wendisch et al., 1998, Microbiology 144, 915-927) and cleaved with the restriction endonuclease HindIII, and the plasmid was checked by subsequent agarose gel electrophoresis.

Figure 1:
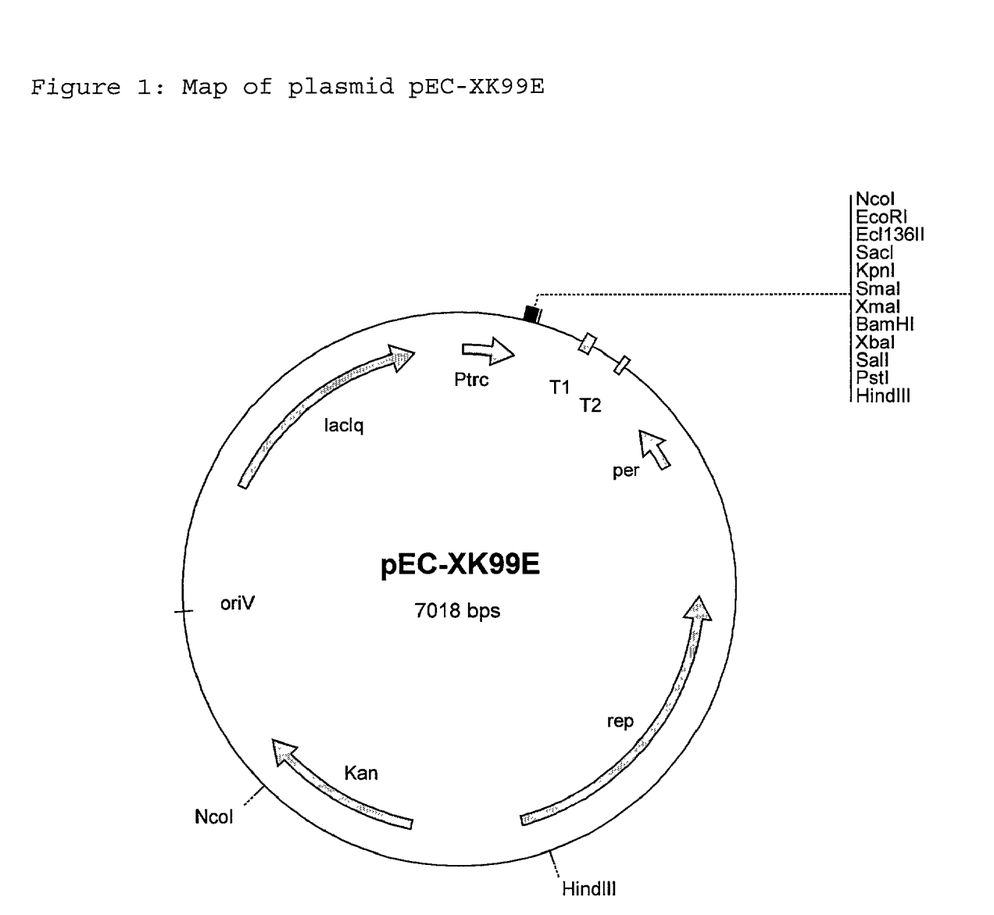

The resulting plasmid construct was called pEC-XK99E (FIG. 1). The strain obtained by the introduction of plasmid pEC-XK99E into the *C. glutamicum* strain DSM5715 by electroporation was called DSM5715/pEC-XK99E and deposited as DSM13455 in the German Collection of Microorganisms and Cell Cultures (DSMZ, Brunswick, Germany) under the terms of the Budapest Treaty.

3.3. Cloning of gpm in *E. coli/C. glutamicum* Shuttle Vector pEC-XK99E

The vector used was the *E. coli/C. glutamicum* shuttle vector pEC-XK99E described in Example 3.2. DNA of this plasmid was fully cleaved with the restriction enzyme Ecl136II and then dephosphorylated with shrimp alkaline phosphatase (Roche Diagnostics GmbH, Mannheim, Germany, product description SAP, product no. 1758250).

The 0.77 kb gpm fragment described in Example 3.1, obtained by means of PCR, was mixed with the prepared vector pEC-XK99E and the mixture was treated with T4 DNA ligase (Amersham Pharmacia, Freiburg, Germany, product description T4 DNA ligase, code no. 27-0870-04). The ligation mixture was transformed to the *E. coli* strain DH5α (Hanahan, in: DNA cloning. A practical approach. Vol. I. IRL-Press, Oxford, Washington DC, USA). Plasmid-carrying cells were selected by plating the transformation mixture on LB agar (Lennox, 1955, Virology 1, 190) containing 25 mg/l of kanamycin. After incubation overnight at 37° C., recombinant single clones were selected. Plasmid DNA was isolated from one transformant with the Qiaprep Spin Miniprep Kit (product no. 27106, Qiagen, Hilden, Germany) in accordance with the manufacturer's instructions and cleaved with the restriction enzymes EcoRI and XbaI in order to check the plasmid by subsequent agarose gel electrophoresis. The plasmid obtained was called pXKgpmexp. It is shown in FIG. 2.

EXAMPLE 4

Transformation of the Strain DSM5715 With Plasmid pXKgpmexp

The strain DSM5715 was transformed with plasmid pXKgpmexp using the electroporation method described by Liebl et al. (FEMS Microbiology Letters 53, 299-303 (1989)). The transformants were selected on LBHIS agar consisting of 18.5 g/l of brain-heart infusion broth, 0.5 M sorbitol, 5 g/l of bacto tryptone, 2.5 g/l of bacto yeast extract, 5 g/l of NaCl and 18 g/l of bacto agar, which had been supplemented with 25 mg/l of kanamycin. Incubation was carried out for 2 days at 33° C.

Plasmid DNA was isolated from one transformant by the conventional methods (Peters-Wendisch et al., 1998, Microbiology 144, 915-927) and cleaved with the restriction endonucleases EcoRI and XbaI, and the plasmid was checked by subsequent agarose gel electrophoresis. The strain obtained was called DSM5715/pXKgpmexp.

The following microorganism was deposited in the German Collection of Microorganisms and Cell Cultures (DSMZ, Brunswick, Germany) under the terms of the Budapest Treaty:

*Corynebacterium glutamicum* strain DSM5715/pXKgpmexp as DSM13456

EXAMPLE 5

Preparation of Lysine

The *C. glutamicum* strain DSM5715/pXKgpmexp obtained in Example 4 was cultivated in a nutrient medium suitable for lysine production and the lysine content of the culture supernatant was determined.

This was done by first incubating the strain on an agar plate with the appropriate antibiotic (brain-heart agar containing kanamycin (25 mg/l)) for 24 hours at 33° C. This agar plate culture was used to inoculate a preculture (10 ml of medium in a 100 ml conical flask). Complete medium CgIII was used as the preculture medium.

| Medium CgIII | |
|---|---|
| NaCl | 2.5 g/l |
| Bacto peptone | 10 g/l |
| Bacto yeast extract | 10 g/l |
| Glucose (autoclaved separately) | 2% (w/v) |

The pH was adjusted to 7.4.

Kanamycin (25 mg/l) was added. The preculture was incubated for 16 hours at 33° C. on a shaker at 240 rpm. This preculture was used to inoculate a main culture to give the latter an initial OD (660 nm) of 0.1. Medium MM was used for the main culture.

| Medium MM | |
|---|---|
| CSL (corn steep liquor) | 5 g/l |
| MOPS (morpholinopropanesulfonic acid) | 20 g/l |
| Glucose (separately autoclaved) | 50 g/l |
| $(NH_4)_2SO_4$ | 25 g/l |
| $KH_2PO_4$ | 0.1 g/l |
| $MgSO_4 \cdot 7H_2O$ | 1.0 g/l |
| $CaCl_2 \cdot 2H_2O$ | 10 mg/l |
| $FeSO_4 \cdot 7H_2O$ | 10 mg/l |
| $MnSO_4 \cdot H_2O$ | 5.0 mg/l |
| Biotin (sterile-filtered) | 0.3 mg/l |
| Thiamine•HCl (sterile-filtered) | 0.2 mg/l |
| L-leucine (sterile-filtered) | 0.1 g/l |
| $CaCO_3$ | 25 g/l |

CSL, MOPS and the salt solution were adjusted to pH 7 with aqueous ammonia and autoclaved. The sterile substrate and vitamin solutions and the dry-autoclaved $CaCO_3$ were then added.

Cultivation is carried out in a volume of 10 ml in a 100 ml conical flask with baffles. Kanamycin (25 mg/l) was added. Cultivation proceeded at 33° C. and 80% atmospheric humidity.

After 72 hours the OD was measured at a wavelength of 660 nm with a Biomek 1000 (Beckmann Instruments GmbH, Munich). The amount of lysine formed was determined with an amino acid analyzer from Eppendorf-BioTronik (Hamburg, Germany) by means of ion exchange chromatography and postcolumn derivatization with ninhydrin detection.

The experimental result in shown in Table 1.

TABLE 1

| Strain | OD (660) | Lysine•HCl g/l |
|---|---|---|
| DSM5715 | 6.8 | 13.68 |
| DSM5715/pXKgpmexp | 7.3 | 14.35 |

What is claimed is:

1. An isolated polynucleotide comprising a polynucleotide sequence selected from the group consisting of:
   (a) a polynucleotide encoding a polypeptide containing the amino acid sequence of SEQ ID NO: 2, the polypeptide having phosphoglycerate mutase activity, and
   (b) a polynucleotide that is fully complementary to the polynucleotide of (a).

2. An isolated corynebacterial polynucleotide comprising a polynucleotide sequence selected from the group consisting of:
   (a) a polynucleotide that is identical to SEQ ID NO: 1 encoding a polypeptide containing the amino acid sequence of SEQ ID NO: 2, the polypeptide having phosphoglycerate mutase activity, and
   (b) a polynucleotide that is fully complementary to the polynucleotide of (a).

3. A member of the coryneform group of bacteria transformed by the polynucleotide according to claims 1 or 2.

4. The bacteria according to claim 3, wherein the bacteria are of the genus *Corynebacterium*.

5. A vector comprising the polynucleotide of claims 1 or 2.

6. The vector of claim 5, wherein said vector is an expression vector.

7. An isolated host cell comprising the vector of claim 5.

8. A host cell of claim 7 that is a prokaryotic cell.

9. An isolated nucleic acid comprising the nucleotide sequence as set forth in SEQ ID NO: 1.

10. The plasmid expression vector pXKgpmexp contained in deposit DSM13456.

* * * * *

UNITED STATES PATENT AND TRADEMARK OFFICE
CERTIFICATE OF CORRECTION

PATENT NO.        : 7,306,939 B2                                              Page 1 of 1
APPLICATION NO.   : 09/725178
DATED             : December 11, 2007
INVENTOR(S)       : Bettina Möckel et al.

It is certified that error appears in the above-identified patent and that said Letters Patent is hereby corrected as shown below:

Claim 1, line 7 (column 17, line 7), replace "fully complementary" with --the full length complement of--.

Claim 2, line 8 (column 17, line 17), replace "fully complementary" with --the full length complement of--.

Signed and Sealed this

Nineteenth Day of August, 2008

JON W. DUDAS
*Director of the United States Patent and Trademark Office*